Jan. 8, 1963 E. B. LE GRICE Plant Pat. 2,209
ROSA FLORIBUNDA PLANT
Filed Jan. 15, 1958
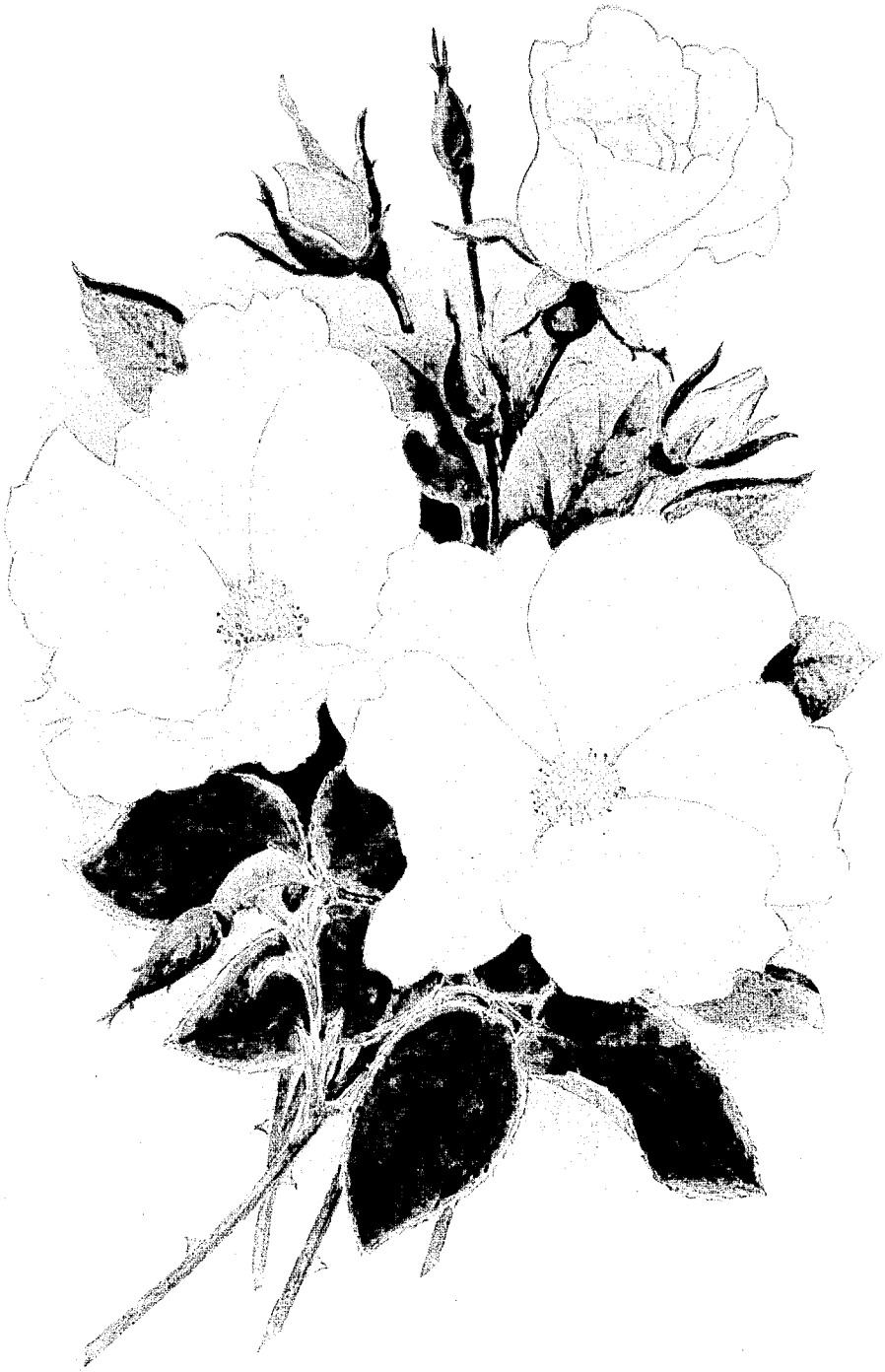
WITNESS
Addison E Avery
INVENTOR
Edward Burton Le Grice,
by John A Leonard,
his ATTY.

United States Patent Office

Plant Pat. 2,209
Patented Jan. 8, 1963

2,209
ROSA FLORIBUNDA PLANT

Edward Burton Le Grice, North Walsham, Norfolk, England

Filed Jan. 15, 1958, Ser. No. 709,127
1 Claim. (Cl. 47—61)

This invention relates to a new variety of rose plant, a Rosa Floribunda hybrid.

The present rose plant was produced originally by the deliberate crossing of a Rosa Floribunda Dainty Maid, an unpatented variety, as a seed parent, with a hybrid tea type rose, Mrs. Sam McGredy, Plant Patent No. 394, as the pollen parent.

The seed parent Dainty Maid was produced by crossing of the rose D. T. Poulsen, an unpatented variety, and an unknown variety.

The ancestry of the pollen parent is unknown.

The new variety was asexually reproduced by me at North Walsham, England, by budding. The new variety has been tested at the National Rose Society's trial grounds at St. Alban's, England.

The drawing shows in color a number of typical stalks with leaves, bud, blooms and thorns.

The exposed plant is in the form of a hardy perennial bush of upright, bushy growth with a flattened top. It is a normally pruned bush, from 3 to 3½ feet high at three years old. It is regular and balanced in shape. It is a vigorous grower.

The exposed portion of the plant has a good resistance to low temperature when protected and unprotected. It has withstood temperatures of 15° F. unprotected. Its resistance both to drought and wet seasons is good.

For growth it prefers moderate sun with a west exposure. It thrives well in any medium loam soil of normal drainage.

The main stalks of the plant grow upright and are slightly branched. For this type of plant, they are relatively stiff and adequate to support the foliage, blooms, and fruit well.

The following color terminology is in accordance with the Horticultural Colour Chart of the Royal Horticultural Society.

The new growth of the stalks ranges from Fern Green, Chart 0862/3, to Pod Green, Chart 061/1, on the exposed side, and Indian Lake, Chart 826/3, on the other side, changing to Rose Madder, Chart 23, near the top.

The old growth is Pod Green, Chart 061/1. On the old growth, the color is relatively uniform. The branches are Pod Green, Chart 061/1.

The main stalks range from 21 inches to 30 inches in length, and are divergent. They have a smooth surface texture with a few prominent thorns.

The branches are whorled, and have smooth bark. They are relatively stiff and variable in quantity, short, and adequate to support the fruit, bloom and foliage well. They are generally Pod Green, Chart 061/1.

The foliage in general is dense and abundant with a whorled leaf arrangement. The new leaves on the top surface range from Lettuce Green, Chart 861/1 and Parsley Green, Chart 962/3, and are edged and veined with Tyrian Rose, Chart 24/1. On the underside they are Tyrian Rose, Chart 24/1.

The old leaves, on the top surface, are Parsley Green, Chart 00962/3, edged and veined with Tyrian Rose, Chart 24/1. On the underside, they are Sage Green, Chart 000861/1.

In general, the color of the old leaves is uniform, and that of the new leaves is variegated.

The leaves are relatively large, ranging to about 7 inches in length and from 4 to 5 inches in width. The leaflets are of the usual shape, being pinnately compound with serrated margins, hastate bases, and acute apices. They are quite thick. On the upper face they are waxy. On the lower face they are smooth. Their persistency on the plant is good. The bold foliage with well spaced leaflets is unusual.

The petioles or leaf stems are a Lettuce Green, Chart 861/2, on the outside, and Rose Madder, Chart 23, on the inside. They average in length to about 2 inches and are strong and smooth.

The stipules are Lettuce Green, Chart 861/2 tipped with Rose Madder, Chart 23.

The plant grows and blooms well in temperate regions. It prefers sun, and a western exposure, and elevations up to 750′ above sea level. It prefers wet and cold seasons, and a well drained, rich loam, slightly acid soil, about pH 6.5. The quality of the blooms improves as optimum conditions are approached. The color is most brilliant under cool conditions. The conditions of temperature, soil, exposures and the like do not much effect the quantity of blooms.

The plant blooms from early June through October, the blooming being continuous for this period of about five months. Cutting of part of the flowers appears not to change the blooming characteristics or period.

The buds are of medium size, and pear shaped, with a waxy aspect. They are borne upright and are terminal and lateral. The petal color, when the sepals first divide, is Carmine, Chart 21. When the petals being to unfurl the color is Carmine, Chart 21/1. When half blown, the color is Carmine, Chart 21/1.

The buds are polysepalous, the sepals being long and slightly fimbriated.

The calyx is normal, being about 1 inch in length and smooth in texture.

The peduncles average from 2 to 8 inches in length and have a waxy surface texture with many tiny thorns. The peduncles generally are Lettuce Green, Chart 861/2. They are strong.

The pedicles average from 1 to 2 inches in length. They are waxy with many tiny thorns. Their color generally is Lettuce Green, Chart 861/2. They are strong.

An increase in the temperature tends to hasten the blooming of the plant.

The blooms are of the single type, normally having five petals each. They average from 4 to 5 inches in diameter and an average plant will bear as many as 20 blooms at the same time. The blooms are borne singly and in racemes. On the plant, they last from four to six days. When cut, they last about four days.

The petalage is generally Carmine, Chart 21/2, ranging into Empire Yellow, Chart 603, at the base of the petals. On the reverse face, the color also is Carmine, Chart 21/2.

The general tonality of the plant from a distance, when it is in bloom, is a Carmine, Chart 21. The Carmine becomes less intense as the bloom ages.

The petals are waxy, thick, wide, and smooth. They are evenly spaced providing well-shaped single type flowers. The petaloids are few or none. The persistence of the petals is good both for cut and uncut blooms. The flower is a true single flower.

The fragrance of the blooms is an average brier perfume. Its lasting quality, both in cut and uncut flowers, is good.

The stamens are simple and numerous. In color, they are Buttercup Yellow, Chart 5/2. The filaments are of medium length and, in color, Buttercup Yellow, Chart 5/2. The pollen is Buttercup Yellow, Chart 5/2. The styles are about ¼ inch and Carmine, Chart 21, and the stigmas are about ½ inch and Buttercup Yellow, Chart 5/2. The stigmas are plentiful.

On the main stalk, from the base of the plant, the thorns are few or occasional. On the laterals from the main stalk, they are numerous and very small. Generally, the thorns are stiff. In color, they are a Rose Madder, Chart 23. The thorns on each type of stalk are evenly distributed. On the peduncles they are evenly distributed.

The drawing further illustrates the characteristics of the variety and the following tabulation is a detailed description of the new variety:

*General*

Parentage:
- *Seed parent.*—Dainty Maid, resulting from a cross between D. T. Poulsen and an unknown rose.
- *Pollen parent.*—A hybrid tea, Mrs. Sam McGredy, of unknown parentage.

Classification: Botanic—Rosa Floribunda hybrid.

*Flower*

Blooming habit:
- *Location where observations were made.*—National Rose Trial Grounds, St. Alban's, England.
- *Flowering.*—Continuous for about five months, from early June until end of October.

Bud:
- *Size.*—Medium.
- *Form.*—Pear shaped.
- *Color.*—When sepals first divide, petals are Carmine, Chart 21, changing to Carmine, Chart 21/1; when petals begin to unfurl they are Carmine, Chart 21/1, and when half blown, they are Carmine 21/1.
- *Sepals.*—Long and slightly fimbriated.
- *Calyx.*—Shape normal, about 1 inch in length, smooth textured.
- *Peduncle.*—Length—from 2 to 8 inches. Aspect—waxy with tiny thorns. Color—Lettuce Green, Chart 861/2. Strength—strong.
- *Opening.*—Rapid, hastened by warmth.

Bloom:
- *Size.*—Four to five inches in diameter.
- *Borne.*—Singly and in racemes.
- *Stems.*—Length, one to two inches, strong. Aspect—waxy, many tiny thorns. Color—Lettuce Green, Chart 861/2.
- *Form.*—When first opened—petals widely open, overlapping at edges, revealing anthers.
- *Permanence.*—On the plant, about four to six days; when cut, about four days.

Petalage:
- *Number of petals under normal conditions.*—5.
- *Color.*—Inside Carmine, Chart 21/2, shaded to Empire Yellow, Chart 603, toward the base of the petal.
- *Variegations.*—The color is about the same on the inside and reverse of the petals, but slightly less intense on the reverse.
- *Discoloration.*—Decreases in intensity with age.

Petals:
- *Texture.*—Waxy and thick.
- *Appearance.*—Great depth of color, each individual petal colored as above.
- *Form.*—Thick, wide and smooth.
- *Arrangement.*—Slightly fimbriated.
- *Petaloids in center.*—Few or none.
- *Persistence.*—Good.
- *Fragrance.*—Average brier perfume.
- *Lasting quality.*—On plant, 4 to 6 days; when cut, 4 days.

Genital organs:
- *Stamens.*—Simple and numerous. Color—Buttercup Yellow, Chart 5/2. Arrangement—regular.
- *Filaments.*—Medium. Color—Buttercup Yellow, Chart 5/2.
- *Pollen.*—Buttercup yellow, Chart 5/2.
- *Styles.*—¼ of an inch, colored Carmine, Chart 21.
- *Stigmas.*—About 1/12 inch, colored Buttercup Yellow, Chart 5/2.
- *Ovaries.*—Plentiful.

Fruit: Usual in form.

*Plant*

Form: A woody bush of upright, bushy growth with flat top.

Growth: Vigorous, about 3 to 3½ feet high at three years.

Foliage: Dense with whorled arrangement.
- *Size.*—Extremely large with length up to 7 inches, width from 4 to 5 inches.
- *Quantity.*—Abundant.
- *Color.*—New leaves, on top, Lettuce Green, Chart 861/1, edged and veined with Tyrian Rose, Chart 24/1. Old leaves, on top, Parsley Green, Chart 00962/3, also edged and veined with Tyrian Rose, Chart 24/1, and on their underside, old leaves are Sage Green, Chart 00861/1.
- *Shape.*—Normal.
- *Texture.*—Upper face—waxy; lower face—smooth, thick.
- *Edge.*—Serrated, edged with Tyrian Rose, Chart 24/1.

Petiole: Length, about 2 inches, strong and smooth. Color—Lettuce Green, Chart 861/2, on the outside, and Rose Madder, Chart 23, on the inside.

Stipules: Lettuce Green, Chart 861, tipped with Rose Madder, Chart 23.

Disease resistance: Appears to have better than average resistance to mildew and blackspot.

Wood:
- *New wood.*—Color, Fern Green, Chart 0862/3 to Pod green, Chart 061/1, on the exposed side with Indian Lake, Chart 826/3, on the other side, changing to Rose Madder, Chart 23, near the top.
- *Old wood.*—Color, Pod Green, Chart 061/1.
- *Bark.*—Smooth.

Thorns:
- *Quantity.*—Few or occasional on main stalks from base, many and very small on laterals.
- *Form.*—Stiff.
- *Color.*—Rose Madder, Chart 23.
- *Position.*—Thorns for each type of stalk, evenly distributed thereon.

The most distinctive features and characteristics of the new hybrid rose plant are its erect and vigorous growth with glossy foliage and widely spaced, branching flower heads and its large leaves, its simple flowers of an unusual shade and size, combining the orange salmon of Mrs. Sam McGredy with the simple vigorous growth of Dainty Maid.

Having shown and described my new variety of Rosa Floribunda plant, and its manner of asexual reproduction, I claim:

The new and distinct variety of Rosa Floribunda plant herein shown and described.

References Cited in the file of this patent

National Rose Society Annual, of England, for 1954, pages 156 and 157.